United States Patent [19]

Hoelderich et al.

[11] Patent Number: 4,777,322

[45] Date of Patent: Oct. 11, 1988

[54] OBTAINING BUT-2-ENES FROM $C_4$-HYDROCARBON MIXTURES WHICH CONTAIN BUT-1-ENE AND MAY OR MAY NOT CONTAIN BUT-2-ENES

[75] Inventors: Wolfgang Hoelderich, Frankenthal; Alfred Lindner, Bobenheim-Roxheim; Wolf D. Mross, Frankenthal; Max Strohmeyer, Limburgerhof; Klaus Volkamer, Frankenthal, all of Fed. Rep. of Germany

[73] Assignee: BASF Aktiengesellschaft, Ludwigshafen, Fed. Rep. of Germany

[21] Appl. No.: 759,234

[22] Filed: Jul. 26, 1985

[30] Foreign Application Priority Data

Jul. 28, 1984 [DE] Fed. Rep. of Germany ....... 3427979

[51] Int. Cl.$^4$ .............................................. C07C 5/23
[52] U.S. Cl. .................................... 585/666; 585/664; 585/667; 585/671
[58] Field of Search ............... 585/664, 666, 667, 670, 585/671

[56] References Cited

U.S. PATENT DOCUMENTS

| 2,403,672 | 7/1946 | Matuszak | 585/664 |
| 3,636,125 | 1/1972 | Hoppstock | 585/666 |
| 3,723,564 | 3/1973 | Tidwell et al. | 585/666 |
| 3,758,604 | 9/1973 | Sprecher et al. | 585/664 |
| 4,104,321 | 8/1978 | Ward | 585/670 |
| 4,410,754 | 10/1983 | Gewartowski | 585/671 |
| 4,503,282 | 3/1985 | Sikkenga | 585/664 |

FOREIGN PATENT DOCUMENTS

| 129899 | 6/1983 | European Pat. Off. | 585/666 |
| 129900 | 6/1983 | European Pat. Off. | 585/666 |
| 1069044 | 5/1967 | United Kingdom | 585/667 |

*Primary Examiner*—Asok Pal
*Attorney, Agent, or Firm*—Keil & Weinkauf

[57] ABSTRACT

But-2-enes are obtained from $C_4$-hydrocarbon mixtures which contain but-1-ene and may or may not contain but-2-enes by catalytic isomerization of the but-1-ene to but-2-enes in an isomerization zone at elevated temperatures by a process in which the isomerization is carried out in combination with a distillative separation zone, the said hydrocarbon mixture being fed to the isomerization zone and/or distillative separation zone, the isomerization mixture obtained from the isomerization zone is passed into the distillative separation zone, a but-1-ene-containing fraction is removed above the lower third of the distillative separation zone and passed into the isomerization zone, and the but-2-enes or a fraction containing these are or is removed in the lower third of the distillative separation zone.

13 Claims, 2 Drawing Sheets

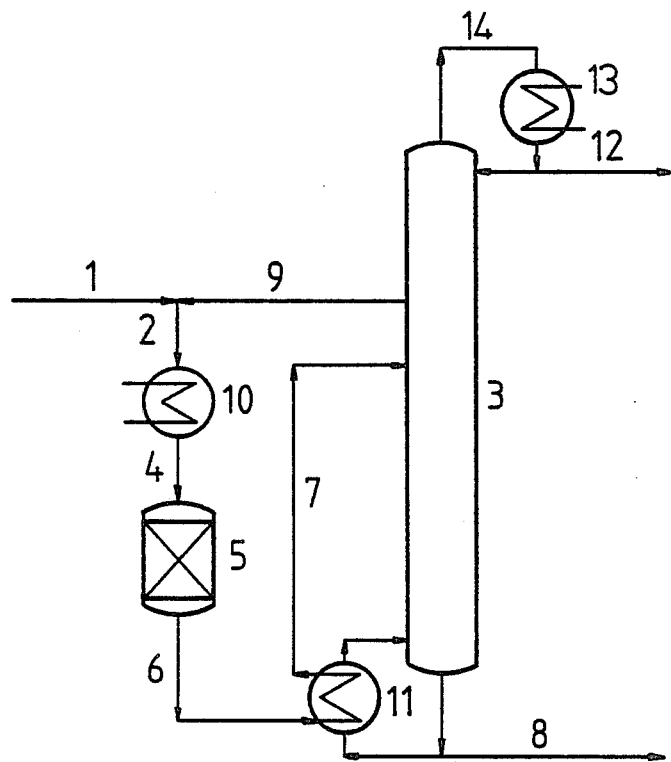

OBTAINING BUT-2-ENES FROM C₄-HYDROCARBON MIXTURES WHICH CONTAIN BUT-1-ENE AND MAY OR MAY NOT CONTAIN BUT-2-ENES

The present invention relates to a process for obtaining but-2-enes from $C_4$-hydrocarbon mixtures which contain but-1-ene and may or may not contain but-2-enes by catalytic isomerization of the but-1-ene to but-2-enes.

It has been disclosed, for example in German Laid-Open Application DOS No. 3,022,821, that but-1-ene can be catalytically isomerized to but-2-enes. However, the conventional processes have the disadvantages that product purity is insufficient, oligomers are formed, the yield is unsatisfactory or the catalyst is difficult to regenerate.

It is an object of the present invention to provide a process for obtaining but-2-enes from $C_4$-hydrocarbon mixtures which contain but-1-ene and may or may not contain but-2-enes by catalytic isomerization of the but-1-ene to but-2-enes, wherein the but-2-ene product can be obtained in good yield and purity.

We have found that this and other objects and advantages are achieved, in accordance with the invention, by a process for obtaining but-2-enes from a $C_4$-hydrocarbon mixture which contains but-1-ene and may or may not contain but-2-enes by catalytic isomerization of the but-1-ene to but-2-enes in an isomerization zone at elevated temperatures wherein the isomerization is carried out in combination with a distillative separation zone, the said hydrocarbon mixture being fed to the isomerization zone and/or distillative separation zone, the isomerization mixture obtained from the isomerization zone is passed into the distillative separation zone, a but-1-ene-containing fraction is removed above the lower third of the distillative separation zone and passed into the isomerization zone, and the but-2-enes or a fraction containing these are or is removed in the lower third of the distillative separation zone.

BRIEF DESCRIPTIONS OF THE DRAWINGS

FIG. 1 is a schematic diagram and illustrates a particular embodiment of the present invention.

FIG. 2 demonstrates the effect of temperature on the composition of the reaction mixture.

In the novel process, the but-2-ene product is obtained in good yield and adequate purity, and the latter can be adjusted to suit the intended use. A particular advantage of the process is that an expensive extractive distillation and the consequent introduction of foreign substances are dispensed with. The specific energy consumption can be kept low by using the heat obtained from the isomerization, for example for preheating the starting $C_4$-hydrocarbon mixture introduced into the isomerization, or for boiling during the distillation. The low temperature level furthermore permits the use of cheap waste heat.

The $C_4$-hydrocarbon mixtures which contain but-1-ene and may or may not contain but-2-enes and are used for the novel process generally contain but-1-ene and, where relevant, but-2-enes in an amount of from 70 to 100, as a rule from 80 to 100, in particular from 90 to 100, % by weight. But-2-ene may be present as cis-but-2-ene or trans-but-2-ene, but as a rule any but-2-ene present in the starting $C_4$-hydrocarbon mixture is in the form of a mixture of cis-but-2-ene and trans-but-2-ene.

In addition to containing the but-2-ene, the said starting mixture may contain as much as 90, as a rule from 1 to 70, in particular from 1 to 60, % by weight of but-2-enes, as well as further $C_4$-hydrocarbons, such as n-butane, isobutane or isobutene.

In the novel process, the said starting $C_4$-hydrocarbon mixture can be fed to the isomerization zone and/or the distillative separation zone, but is advantageously fed to the latter zone, for example to the lower or, preferably, middle third of this zone, when the starting $C_4$-hydrocarbon mixture already contains but-2-enes in addition to the but-1-ene, for example in a concentration which is higher than the concentration of but-2-enes established in the isomerization zone. Even if the starting $C_4$-hydrocarbon mixture contains, in addition to small amounts of but-1-ene, predominantly butanes and but-2-enes, and it is desired to separate the butanes from the but-2-ene or to reduce the concentration of the butanes in order to obtain a substantially butane-free but-2-ene product, the starting $C_4$-hydrocarbon mixture is preferably fed into the distillative separation zone. On the other hand, if the starting $C_4$-hydrocarbon mixture has a high content of but-1-ene, eg. not less than 20, in particular not less than 30, % by weight, the said mixture is generally fed to the isomerization zone.

Where the starting $C_4$-hydrocarbon mixture contains not only but-1-ene and possibly but-2-enes but also n-butane, and it is desired to separate off the n-butane in order to obtain a but-2-ene product having a lower n-butane concentration, it may be advantageous if a but-1-ene-containing fraction which additionally contains trans-but-2-ene is removed above the lower third of the distillative separation zone and recycled to the isomerization zone, and at the same an n-butane-containing fraction is removed from the distillative separation zone, advantageously at a point above the lower third of the distillative separation zone. This procedure makes it possible to obtain a but-2-ene product which has a greatly reduced n-butane concentration, although the boiling points of n-butane and trans-but-2-ene differ only slightly. In general, the amount of trans-but-2-ene recycled to the isomerization zone is such that the weight ratio of trans-but-2-ene recycled to the isomerization zone to n-butane removed is advantageously from 100:1 to 1:100, preferably from 50:1 to 1:50, in particular from 10:1 to 1:10.

The isomerization can be carried out in one or more stages, but in general one stage is employed. However for obtaining low-butane but-2-ene products, it may be advantageous to employ a plurality of isomerization stages, eg. 2 or 3.

Advantageously, acidic catalysts are used as catalysts for the isomerization of the but-2-enes to but-1-ene. The acidic catalysts may be used in the liquid phase, for example in the form of aqueous mineral acids, preferably aqueous phosphoric acids, eg. phosphoric acids containing from 1 to 80, preferably from 2 to 75, % by weight of $P_2O_5$, or in the form of solid catalysts.

Examples of advantageous solid acidic catalysts are solid phosphoric acid catalysts which contain monophosphoric or preferably polyphosphoric acid on a solid carrier. Examples of suitable carriers for the phosphoric acid catalysts are alumina, silica, active carbon, kieselguhr or pumice. Silica gel is preferably used as the carrier.

Other suitable acidic catalysts are acidic metal sulfates, such as sodium bisulfate, calcium bisulfate, aluminum sulfates, nickel sulfate, copper sulfate, cobalt sulfate, cadmium sulfate or strontium sulfate. These acidic metal sulfates can be used as such but are preferably employed on a carrier, examples of suitable carriers being silica gel, active carbon, alumina and pumice.

Silica gel or alumina alone is also suitable.

Particularly advantageously used acidic catalysts are zeolites of the pentasil type. These zeolites may have different chemical compositions, and may be aluminosilicate, borosilicate, iron silicate, gallium silicate, chromium silicate, arsenosilicate and bismuth silicate zeolites and mixtures of these, and aluminogermanate, borogermanate, gallium germanate and iron germanate zeolites and mixtures of these. For example, the aluminosilicate zeolites are crystalline aluminosilicates which possess a highly ordered structure with a rigid three-dimensional network of $SiO_4$ and $AlO_4$ tetrahedra which are linked through common oxygen atoms. The ratio of Si and Al atoms to oxygen is 1:2. The electrovalency of the aluminum-containing tetrahedra is balanced by the incorporation of cations into the crystal, for example an alkali metal ion or a hydrogen ion. Cation exchange is possible. The spaces between the tetrahedra are occupied by water molecules prior to dehydration by drying or calcination. The other zeolites mentioned above in addition to the aluminosilicate zeolites are crystalline compounds which have a zeolite structure and in which, instead of the aluminum, trivalent elements such as B, Fe, Ga, Cr, As or Bi, and, instead of the silicon, tetravalent elements such as Ge are incorporated in the zeolite framework.

Aluminosilicate, borosilicate and iron silicate zeolites of the pentasil type are particularly useful as catalysts for the novel process.

The aluminosilicate zeolites are prepared, for example, by a method in which an aluminum compound, preferably an aluminum hydroxide, such as $Al(OH)_3$, or an aluminum salt, such as aluminum sulfate, is reacted with a silicon component, advantageously silica, preferably in a finely divided form, expediently in a liquid medium, with or without the addition of an alkali metal and/or an alkaline earth metal, at elevated temperatures, in general at from 100° to 220° C., advantageously under autogenous pressure. Examples of suitable aqueous media for the preparation of the zeolites are water on its own, aqueous alkali metal hydroxide solutions, alcohols, such as methanol, ethanol, propanol, butanol, ethylene glycol or butane-1,4-diol, if appropriate mixed with water, and ethers, such as ethylene glycol monomethyl ether, ethylene glycol dimethyl ether, diethylene glycol monomethyl ether or diethylene glycol dimethyl ether, if appropriate mixed with water, and preferably amines, such as 1,6-hexanediamine, 1,3-propanediamine or triethylenetetramine, advantageously mixed with water. Depending on the amounts of starting materials chosen, the resulting aluminosilicate zeolites have an $SiO_2/Al_2O_3$ ratio of from 10 to 40,000.

The borosilicate zeolites of the pentasil type can be prepared, for example, by a method similar to that described above for the preparation of the aluminosilicate zeolites, by reacting a boron compound, eg. $HBO_3$, instead of the aluminum compound, with the silicon compound. Preferably used reaction temperatures in this procedure are from 90° to 200° C.

The iron silicate zeolites of the pentasil type can, for example, also be prepared by a method similar to that described above for the preparation of the aluminosilicate zeolites, by reacting an iron compound, preferably $Fe_2(SO_4)_3$, instead of the aluminum compound, with the silicon compound. Preferably used reaction temperatures here are from 100° to 220° C.

Further processing of the resulting aluminosilicate, borosilicate and iron silicate zeolites to give the catalyst employed is carried out, for example, in the following manner: the said zeolites are isolated, dried at in general from 80° to 160+ C., preferably from 100° to 120° C., calcined at, advantageously, from 450° to 550° C., preferably from 490° to 510° C., and then advantageously molded with a binder in a weight ratio of in general from 90:10 to 40:60 to give, for example, extrudates, pellets or tablets. Examples of suitable binders are aluminas, preferably boehmite, aluminosilicates, advantageously in amorphous form and having an $SiO_2/Al_2O_3$ ratio of in general from 25:75 to 95:5, preferably from 1:1 to 10:1, in particular about 75:25, silica, preferably in finely divided form, mixtures of silica, which is advantageously finely divided, and finely divided alumina, and titanium dioxide, advantageously finely divided, and clay. After the molding procedure, the extrudates or pellets are advantageously dried, as a rule for from 10 to 20, eg. about 16, hours, in general at from 80° to 160° C., preferably from 100° to 120° C., and are then calcined, in general for from 10 to 20, eg. 16, hours, advantageously at from 450° to 550° C., preferably from 490° to 520° C.

In another embodiment for further processing to give the catalyst employed, the aluminosilicate, borosilicate or iron silicate zeolite isolated is molded directly after being dried, and is subjected to calcination only after the molding procedure.

However, the aluminosilicate, borosilicate and iron silicate zeolites obtained can also be molded in pure form, ie. without a binder, and can be employed as, for example, extrudates, tablets, pellets or fluidized material.

If the zeolite is obtained in the synthesis not in the catalytically active acidic H form but in, for example, the Na form, the latter can be completely or partially converted to the desired H form by ion exchange with ammonium ions followed by calcination or by treatment with an acid.

To increase the selectivity, the catalyst life and the number of possible regenerations, the zeolite catalysts used according to the invention can be modified in various ways.

In one method of modifying the catalysts, the unmolded or molded zeolites are subjected to ion exchange, or are doped, with alkali metals, such as Na, alkaline earth metals, such as Ca or Mg, earth metals, such as B or Tl, and preferably transition metals, such as Mn, W, Fe, Mo, Cu or Zn, noble metals, such as Pd, and/or rare earth metals, such as La or Ce. In an embodiment of this modification, for example, the molded pentasil zeolite is initially taken in a syphon tube, and a salt of one of the metals described above, eg. a halide or a nitrate, advantageously in aqueous solution, is passed over the zeolite at room temperature or elevated temperatures, eg. from 20° to 120° C., preferably from 20° to 100° C. Ion exchange of this type can be carried out on, for example, the hydrogen, ammonium or alkali metal form of the zeolite. In another embodiment of the method of modification, the zeolite material is impregnated with a compound of one of the metals described above, eg. a halide, nitrate and/or oxide, in a liquid medium, for example in aqueous or alcoholic solution. Both ion exchange and impregnation are advantageously followed by one or more drying and/or calcination steps. In another embodiment of the method of modification, for example, a pure pulverulent zeolite is suspended in a stirred ammoniacal solution of a salt of the metal to be applied, for example in an ammoniacal Pd(NO$_3$)$_2$ solution, at from 20° to 120° C., preferably from 40° to 100° C., advantageously for from 6 to 30, eg. about 24, hours. The zeolite material obtained by filtration, drying at in general from 120° to 180° C., preferably from 140° to 160° C., and calcination at in general about 450°–550° C., preferably from 480° to 520° C., can be further processed with or without a binder to give molded particles, for example extrudates or pellets. In another embodiment of the method of modification, the H form of the particular zeolite is subjected to ion exchange by, for example, initially taking the molded zeolite (for example in the form of extrudates or pellets) in a column, and circulating over it an ammoniacal solution of a salt of the metal to be applied, for example an ammoniacal Pd(NO$_3$)$_2$ solution, at slightly elevated temperatures, in general at from 30° to 80° C., advantageously for from 10 to 25, preferably from 15 to 20, hours. The product is then advantageously washed thoroughly with water, dried, at, for example, about 150° C. and calcined at, for example, 550° C. In the case of the metal-doped zeolites, it may be advantageous if these steps are followed by aftertreatment with hydrogen.

In another possible method of modification, the molded or unmolded zeolite material is treated with an acid, such as hydrochloric acid, hydrofluoric acid or phosphoric acid and/or with steam. Moreover, the activity of the catalyst can be adjusted to give optimum selectivity with respect to the desired product by partial precoking.

In another embodiment of the novel process, the acidic catalyst used for the isomerization is a metal phosphate, in particular a metal hydrogen phosphate. These phosphates can also contain phosphoric acid in an excess over and above the stoichiometric composition of the acidic metal phosphates, for example in an excess as high as 65%, preferably as high as 20%, in particular as high as 10%. Examples of suitable metal phosphates of this type are magnesium phosphates, calcium phosphates, strontium phosphates, barium phosphates, manganese phosphates, nickel phosphates, copper phosphates, cobalt phosphates, cadmium phosphates, iron(II) phosphates, chromium phosphates and in particular aluminum phosphates. The metal phosphate catalyst can be used as such or on a carrier, examples of suitable carriers being alumina, silica, active carbon and zinc oxide.

Where the activity of the solid acidic catalyst decreases, the catalyst is advantageously regenerated. In an advantageous method of regenerating the solid catalysts, the catalyst is treated with phosphoric acid, preferably aqueous phosphoric acid. This treatment can be carried out continuously, ie. without interrupting the isomerization reaction, by adding, advantageously, aqueous phosphoric acid to the catalyst during the isomerization, advantageously at about the isomerization temperature. The phosphoric acid is added in general in an amount such that from $10^{-6}$ to $10^{-3}$, preferably from $10^{-5}$ to $10^{-4}$, kg/hour, based on the catalyst and calculated as P$_2$O$_5$, of P$_2$O$_5$ is introduced per kg of catalyst. The solid catalyst may also be regenerated batchwise, ie. by interrupting the isomerization reaction. Batchwise isomerization is likewise advantageously effected at elevated temperatures, eg. at from 50° to 300° C., preferably from 50° to 250° C., in particular from 50° to 150° C., phosphoric acid generally being added to the catalyst in an amount such that about 0.1–20% by weight, based on the catalyst and calculated as P$_2$O$_5$, of P$_2$O$_5$ are added. In general, treatment of the solid catalyst with phosphoric acid is carried out by allowing the phosphoric acid, advantageously aqueous phosphoric acid, to trickle over the catalyst.

Furthermore, the solid acidic catalyst, in particular the zeolite catalyst, can advantageously be regenerated by combustion with oxygen-containing gases, preferably air. It may be advantageous to dilute the air with an inert gas, eg. nitrogen. The treatment of the catalysts with the oxygen-containing gases is generally carried out at from 300° to 600° C., preferably from 400° to 550° C., in particular from 480° to 520° C. In this way, the initial activity of the catalyst can be regained in a simple manner.

The novel process has the advantage that there is no need to add steam to the but-1-ene-containing C$_4$-hydrocarbon mixture passed into the isomerization zone. Although the C$_4$-hydrocarbon mixture to be isomerized may also be diluted with steam, the amount of steam added to the said mixture is as a rule restricted to less than 1, preferably not more than 0.8, in particular not more than 0.5, mole of water per mole of but-1-ene.

The catalysts described here can be employed alternatively in the form of extrudates, eg. from 2 to 4 mm extrudates, tablets, eg. tablets having a diameter of from 3 to 5 mm, powders, eg. those having particle sizes of from 0.1 to 0.5 mm, pellets, eg. pellets having a diameter of from 2 to 5 mm, or fluidizable catalytic material.

The amount of acidic catalyst is in general about 0.01–10, preferably about 0.03–2, kg per kg/h of the but-1-ene, passed through the reactor, to be isomerized. Preferably, the isomerization is carried out using fixed-bed reactors.

The isomerization of the but-1-ene to but-2-enes in the isomerization zone is effected in general at from 80° to 400° C., preferably from 100° to 350° C., in particular from 150° to 250° C. The isomerization may be carried out under atmospheric pressure but is preferably effected under superatmospheric pressure, advantageously under pressures as high as 100, preferably from 2 to 60, in particular from 6 to 40, bar.

The isomerization mixture obtained from the isomerization zone is then passed into the distillative separation zone to separate the but-2-enes from but-1-ene, a but-1-ene-containing fraction being removed above the lower third of the distillative separation zone, in general in the upper half of this zone, and being recycled to the isomerization zone. Any isobutane and/or isobutene present in the isomerization mixture is advantageously taken off in the upper half, preferably in the upper third, in particular at the top, of the distillative separation zone. In general, conventional distillation columns, having, for example, about 100 trays are used for the distillative separation.

Drawing FIG. 1 is a schematic flow diagram and illustrates a particular embodiment of the present invention. Referring to FIG. 1, the starting C$_4$-hydrocarbon mixture which contains but-1-ene and may or may not contain but-2-enes is fed into the isomerization reactor 5 via lines 1, 2 and 4 and after being preheated in heat exchanger 10. The isomerization mixture obtained from the isomerization zone 5 is fed to distillation column 3 via lines 6 and 7 and is cooled beforehand in reboiler 11 for distillation column 3. A but-1-ene-containing fraction is taken off from the distillation column and recycled via lines 9, 2 and 4 into the isomerization reactor, in which isomerization of the but-1-ene to the but-2-enes is effected over an acidic catalyst.

The but-2-enes are removed from the bottom of the distillation column 3 via line 8. Isobutane present in the starting C$_4$-hydrocarbon mixture is removed at the top of the distillation column 3 via line 12, after passing through the isomerization reactor. The top product of column 3 is taken off via line 14 and fed to condenser 13. The liquefied reflux is recycled to the distillation column 3, and the top product is removed via line 12 in gaseous or liquid form.

But-2-enes are important starting materials, for example for the preparation of 2-methylbutanal.

The Examples which follow illustrate the invention.

EXAMPLE 1

The Table below shows conversion and selectivities achieved using various catalysts for the isomerization of but-1-ene to cis-but-2-ene and trans-but-2-ene. The reactions were carried out under isothermal conditions in a tube reactor (0.6 cm internal diameter, 90 cm length) in the gas phase. Quantitative and qualitative determination of the product mixture was effected by gas chromatography. The catalysts used were prepared as follows:

Catalyst A

The aluminosilicate zeolite of the pentasil type was synthesized under hydrothermal conditions under autogenous pressure and at 150° C. from 65 g of finely divided SiO$_2$, 20.3 g of Al$_2$(SO$_4$)$_3$.18H$_2$O in 1 kg of 50% strength by weight aqueous 1,6-hexanediamine solution in a stirred autoclave. The crystalline product was filtered off, washed thoroughly and then dried for 24 hours at 110° C. and calcined for 24 hours at 500° C. This aluminosilicate zeolite contained 91.6% by weight of SiO$_2$ and 4.6% by weight of Al$_2$O$_3$.

Catalyst B

The borosilicate zeolite of the pentasil type was synthesized under hydrothermal conditions from 64 g of finely divided SiO$_2$ and 12.2 g of H$_3$BO$_3$ in 800 g of a 50% strength by weight aqueous 1,6-hexanediamine solution at 170° C. and under autogenous pressure in a stirred autoclave. The crystalline product was filtered off, washed thoroughly and then dried for 24 hours at 100° C. and calcined for 24 hours at 500° C. This borosilicate zeolite was composed of 94.2% by weight of SiO$_2$ and 2.32% by weight of B$_2$O$_3$.

This material was converted to 2 mm extrudates by molding with boehmite in a weight ratio of 60:40, and the resulting extrudates were dried for 16 hours at 110° C. and calcined for 24 hours at 500° C.

Catalyst C

Catalyst C was prepared from an iron silicate zeolite by molding it with boehmite in a weight ratio of 60:40 to give extrudates and then calcining the latter for 16 hours at 500° C. The iron silicate zeolite of the pentasil type was synthesized under hydrothermal conditions under autogenous pressure and at 165° C. from 273 g of waterglass, dissolved in 253 g of a 50% strength by weight aqueous 1,6-hexanediamine solution, 31 g of iron sulfate, dissolved in 21 g of 96% strength by weight sulfuric acid, and 425 g of water in a stirred autoclave in the course of 4 days. Thereafter, the product was filtered off, washed thoroughly, dried for 24 hours at 100° C. and calcined for 24 hours at 500° C. This iron silicate zeolite had an SiO$_2$/Fe$_2$O$_3$ ratio of 17.7 and contained 0.62% by weight of Na$_2$O.

Catalyst D

An ammoniacal Pd(NH$_3$)$_4$(NO$_3$)$_2$ solution was circulated over catalyst B (65 ml/min). The product was thendried at 110° C. and calcined at 500° C. The Pd content of the resulting catalyst was 3.3% by weight.

Catalyst E

Catalyst B was subjected to ion exchange with a 20% strength by weight NaCl solution at 80° C. Calcination at 500° C. gave a catalyst containing 0.28% by weight of Na.

Catalyst F

Catalyst B was impregnated with Mg acetate for about 30 minutes, and the product was dried at 130° C. and calcined at 540° C. The Mg content of the resulting catalyst was 1.88% by weight.

Catalyst G

Catalyst B was impregnated with Ba(OH)$_2$.8H$_2$O for about 30 minutes, and the product was dried at 130° C. and calcined at 540° C. The Ba content of the resulting catalyst was 3.1% by weight.

Catalyst H

Catalyst B was impregnated with Zn(NO$_3$)$_2$.6H$_2$O for about 30 minutes, and the product was dried at 130° C. and calcined at 540° C. The zn content of the resulting catalyst was 3.4% by weight.

Catalyst I

Catalyst B was impregnated with Cd(NO$_3$)$_2$.4H$_2$O for about 30 minutes and the product was dried at 130° C. and calcined at 540° C. The Cd content of the resulting catalyst was 6.4% by weight.

Catalyst J

Catalyst B was impregnated with Fe(NO$_3$)$_2$.9H$_2$O for about 30 minutes, and the product was dried at 130° C. and calcined at 540° C. The Fe content of the resulting catalyst was 3.3% by weight.

Catalyst K

Catalyst B was impregnated with Co(NO$_3$)$_2$.6H$_2$O for about 30 minutes, and the product was dried at 130° C. and calcined at 540° C. The Co content of the resulting catalyst was 3.8% by weight.

Catalyst L

Catalyst B was impregnated with Ni(NO$_3$)$_2$.6H$_2$O for about 30 minutes, and the product was dried at 130° C. and calcined at 540° C. The Ni content of the resulting catalyst was 3.7% by weight.

TABLE

Isomerization of but-1-ene to but-2-ene at a reaction temperature of 200° C. and a space velocity (WHSV) of 1 h$^{-1}$

| Catalyst | A | B | C | D | E | F | G | H | I | J | K | L |
|---|---|---|---|---|---|---|---|---|---|---|---|---|
| Product composition, % by weight | | | | | | | | | | | | |
| But-1-ene | 15.7 | 14.8 | 25.0 | 14.54 | 50.4 | 20.51 | 17.42 | 17.28 | 23.03 | 15.06 | 15.72 | 14.75 |
| Cis-but-2-ene | 33.2 | 33.4 | 31.1 | 31.33 | 20.4 | 29.96 | 30.81 | 30.51 | 29.76 | 30.74 | 30.54 | 31.42 |
| Trans-but-2-ene | 50.5 | 51.4 | 43.4 | 53.65 | 28.7 | 48.94 | 51.21 | 51.48 | 46.8 | 52.98 | 52.41 | 52.98 |

EXAMPLE 2

Drawing FIG. 2 demonstrates the effect of temperature on the composition of the reaction mixture when catalyst B is used, at a space velocity of 1 h$^{-1}$. In FIG. 2, C=concentration in % by weight,
T=temperature in °C.,
B2T=trans-but-2-ene,
B2C=cis-but-2-ene and
B1=but-1-ene

EXAMPLE 3

The procedure described in Example 1 was followed, except that the reacted mixture obtained from the isomerization reactor was distilled in a distillation column, and the but-1-ene-containing top product from the distillation was recycled to the feed for the isomerization. Virtually but-1-ene-free but-2-ene product was taken off as a bottom product of the distillation. In this procedure, but-2-ene was obtained in a yield of virtually 100%.

When 10% of butane was mixed with the but-1-ene employed, the butane collected in the upper part of the distillation column, and the major part of it was separated off. The butane content of the but-2-ene product removed at the bottom of the distillation column was sufficiently low to permit the product to be used, for example, for a subsequent carbonylation reaction.

We claim:

1. A process for obtaining butenes-2 from a C$_4$-hydrocarbon mixture which contains butene-1 and n-butane and may or may not contain butenes-2, comprising
   (a) feeding the starting C$_4$-hydrocarbon mixture to the isomerization zone and/or distillative separation zone;
   (b) isomerizing the butene-1 in an isomerization zone in the presence of an acidic catalyst at from 100° to 350° C.;
   (c) passing the isomerization mixture obtained from the isomerization zone into a distillation separation zone;
   (d) removing a butene-1-containing fraction which additionally contains trans-butene-2 above the lower third of the distillative separation zone, and passing it to the isomerization zone;
   (e) removing at the same time an n-butane-containing fraction from the distillative separation section at a point above the lower third of the distillative separation zone; and
   (f) removing the butenes-2 or a fraction containing these in the lower third of the distillative separation zone.

2. A process as claimed in claim 1, wherein an acidic catalyst is employed for the isomerization.

3. A process as claimed in claim 1, wherein phosphoric acids and/or phosphates-containing catalysts are used.

4. A process as claimed in claim 1, wherein the catalyst used is one which contains a zeolite of the pentasil type.

5. A process as claimed in claim 1, wherein a catalyst containing an aluminosilicate zeolite is used.

6. A process as claimed in claim 1, wherein a catalyst containing a borosilicate zeolite is used.

7. A process as claimed in claim 1, wherein a catalyst containing an iron silicate zeolite is used.

8. A process as claimed in claim 1, wherein the catalyst used is a zeolite doped with transition metals.

9. A process as claimed in claim 1, wherein the catalyst used is a zeolite doped with noble metals.

10. A process as claimed in claim 1, wherein a catalyst doped with rare earth metals is used.

11. A process as claimed in claim 9, wherein a palladium-doped zeolite is used as the catalyst.

12. A process as claimed in claim 1, wherein the isomerization is carried out in the presence of hydrogen.

13. A process as claimed in claim 1, wherein the amount of transbutene-2 recycled to the isomerization zone in step (d) is such that the weight ratio of trans-butene-2 recycled to the isomerization zone to n-butane removed in step (d) is from 100:1 to 1:100.

* * * * *